United States Patent [19]
Weiler

[11] 3,969,357
[45] July 13, 1976

[54] 3-PYRIDYLMETHYL PHENYL UREA METAL SALT COMPLEXES

[75] Inventor: Ernest D. Weiler, Ambler, Pa.

[73] Assignee: Rohm and Haas Company, Philadelphia, Pa.

[22] Filed: May 28, 1974

[21] Appl. No.: 473,594

[52] U.S. Cl. .................. 260/270 PY; 260/295 E; 260/294.8 G; 260/294.9; 424/245; 424/263; 424/84

[51] Int. Cl.² .................. C07F 3/04; C07F 3/06; C07F 3/08; C07F 15/06

[58] Field of Search... 260/270 PY, 295 E, 294.8 G, 260/294.9; 71/94; 424/245

[56] References Cited
UNITED STATES PATENTS

| | | | |
|---|---|---|---|
| 3,128,280 | 4/1964 | Rong | 260/295 E |
| 3,700,678 | 10/1972 | Mihailovski | 260/295 E |
| 3,931,203 | 1/1976 | Kilbourn et al. | 260/249.9 |

OTHER PUBLICATIONS
Ware et al., Chem. Abs. 82, 4130h, (1975).

*Primary Examiner*—Alton D. Rollins
*Assistant Examiner*—Mark L. Berch

[57] ABSTRACT

Novel metal salt complexes of 3-pyridylmethyl 4-substituted-phenyl ureas which are rodenticides. The most preferred compounds are derived from zinc chloride.

13 Claims, No Drawings

3-PYRIDYLMETHYL PHENYL UREA METAL SALT COMPLEXES

This invention is concerned with novel metal salt complexes of 3-pyridylmethyl 4-substituted-phenyl ureas which are biologically active.

The novel metal salt complexes may be depicted by the structure

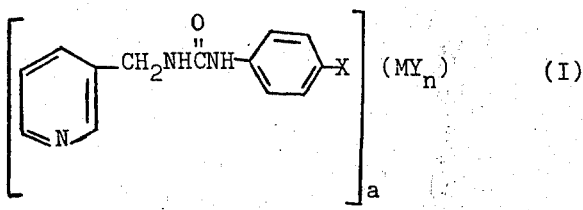

wherein

X is (a) —C(O)R$_1$ wherein R$_1$ is methyl, ethyl or propyl, (b) —SR$_2$ wherein R$_2$ is alkyl of 1 to 4 carbon atoms, (c) cyano or (d) nitro;

M is a cation of a metal selected from the group consisting of cadmium, calcium, cobaltous, cupric, nickelous and zinc;

Y is a halide anion;

$a$ is the integer 2 except when M is cadmium in which case $a$ is 1; and $n$ is an integer corresponding to the valence of M.

The preferred compounds are those corresponding to Formula II

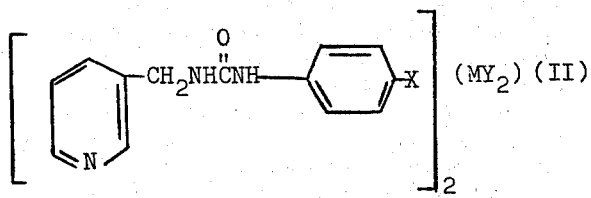

wherein

X is —C(O)C$_3$H$_7$—$n$, —CN, —NO$_2$ or —SCH$_3$;

M is calcium, cobaltous, cupric or zinc ion; and

Y is bromide or chloride,

The most preferred salt for MY$_2$ is zinc chloride.

The compounds of this invention are particularly useful as rodenticides. The 1-(3-pyridylmethyl)-3-(4'-substituted-phenyl)-urea moiety of these metal salt complexes are rodenticidal. The metal salt complex derivatives do, however, have advantages. They are distinct chemical compounds which possess increased stability over their urea moieties.

As a rule the metal salt complex has a higher melting point than its corresponding urea and this is partly responsible for the increased stability of the metal salt complex. When the parent urea degrades, for example upon being subjected to heat, it at least in part may revert to its components 3-pyridylmethylamine and a 4-substituted aniline. The presence of impurities of this type have been known to render a rodenticidal bait less acceptable by the rodent. Accordingly any means of rendering an active rodenticide of this urea type more stable without seriously affecting its toxicity to the rodents is desirable, and the metal salt complexes of this invention accomplish this.

Also it appears that by means of the metal salt complexes of this invention, a slow release of the basic 1-(3-pyridylmethyl)-3-(4'-substituted-phenyl)urea is achieved. This becomes advantageous when single-dose rodenticides which give a relatively rapid kill are involved. After the rodent has eaten a lethal dose it is desirable that he has time to return to his home base before becoming too incapacitated to move. In this manner the rodent will die away from the bait surroundings and the dead carcasses will not become an unsightly nuisance.

The relatively high melting point of each metal salt complex of this invention allows the technical product to be easily tabletized and/or formulated without danger of decomposition into its component parts.

The 3-pyridylmethyl 4-substituted-phenyl urea metal salt complexes of this invention are readily made by allowing a solution of a 3-pyridylmethyl 4-substituted-phenyl urea to react with a solution of the appropriate metal salt. The preferred solvents are alcohols such as methanol, ethanol, isopropanol and 2-methoxyethanol. However, any solvent in which the reactants have a solubility of at least 5% and which are inert may be used. Anhydrous conditions are preferred and the anhydrous grade of the metal salt is almost always used. It is often necessary to warm the metal salt or the 1-(3-pyridylmethyl)-3-(4-substituted-phenyl)-urea and the solvent to achieve solution. Temperatures up to 100°C. are quite satisfactory and the reaction may be carried out without cooling if desired. The reaction may be run in the temperature range of 0°–100°C., although ambient temperatures are usually preferred. The product often precipitates as the reaction proceeds or upon cooling and may be isolated by filtration. In cases where the reaction product is soluble in the reaction solvent, isolation is achieved by partial or complete evaporation of the solvent.

The following examples illustrate the preferred methods of preparation.

EXAMPLE 1

Preparation of 1-(3-pyridylmethyl)-3-(4-butyrylphenyl)urea zinc chloride complex To a solution of 1-(3-pyridylmethyl)-3-(4-butyrylphenyl)urea (2.98 g., 0.01 mole) in 200 ml. of methanol was added a solution of anhydrous zinc chloride (0.68 g., 0.005 mole) in 50 ml. of methanol. After standing overnight the solution was concentrated in vacuo to give 2.3 g. of white solid. This was a 63% yield of 1-(3-pyridylmethyl)-3-(4-butyrylphenyl)urea zinc chloride complex.

EXAMPLE 2

Preparation of
1-(3-pyridylmethyl)-3-(4-cyanophenyl)urea zinc chloride complex

To a solution of 1-(3-pyridylmethyl)-3-(4-cyanophenyl)urea (2.52 g., 0.01 mole) in 100 ml. of methanol was added anhydrous zinc chloride (0.68 g., 0.005 mole) dissolved in 50 ml. of methanol. A solid suspension formed and after stirring 1 hr. the solid was filtered off and air dried. The product was 2.33 g. which was a 72% yield of 1-(3-pyridylmethyl)-3-(4-cyanophenyl)urea zinc chloride complex.

Table II gives the analytical data calculated and found for these examples.

Table I

| | [3-Pyridylmethyl—NHC(O)NHC$_6$H$_4$—X-4]$_a$(MY$_n$) Compounds | | | | | |
|---|---|---|---|---|---|---|
| Example | X | a | M$^{++}$ | Y | n | Melting Point (°C.) |
| 1 | —C(O)C$_3$H$_7$-n | 2 | Zn | Cl | 2 | 167–172 (slow dec.) |
| 2 | —CN | 2 | Zn | Cl | 2 | 223–226 (dec.) |
| 3 | —NO$_2$ | 2 | Ca | Cl | 2 | >260 |
| 4 | —NO$_2$ | 1 | Cd | Cl | 2 | >280 |
| 5 | —NO$_2$ | 2 | Co | Cl | 2 | 218–220 |
| 6 | —NO$_2$ | 2 | Cu | Cl | 2 | 222–228 (dec.) |
| 7 | —NO$_2$ | 2 | Zn | Br | 2 | 234–238 |
| 8 | —NO$_2$ | 2 | Zn | Cl | 2 | 231–232 |
| 9 | —SCH$_3$ | 1 | Cd | Cl | 2 | >260 |
| 10 | —SCH$_3$ | 2 | Cu | Cl | 2 | 208–210 |
| 11 | —SCH$_3$ | 2 | Zn | Cl | 2 | 208–210 |

Table II

Analytical Data on Examples

| Example | Empirical Formula | %C | %H | %N | Analysis* %S | %Cl | % Metal |
|---|---|---|---|---|---|---|---|
| 1 | C$_{17}$H$_{19}$N$_3$O$_2$.1/2ZnCl$_2$ | 55.6(55.9) | 5.3(5.2) | 11.7(11.5) | — | — | — |
| 2 | C$_{14}$H$_{12}$N$_4$O.1/2ZnCl$_2$ | 51.9(52.5) | 3.9(3.8) | 17.6(17.5) | — | — | — |
| 3 | C$_{13}$H$_{12}$C$_4$O$_3$.1/2CaCl$_2$.2H$_2$O | 39.5(42.9) | 3.8(4.4) | 14.4(15.4) | — | 9.0(9.8) | Ca 4.7 (5.5) |
| 4 | C$_{13}$H$_{12}$N$_4$O$_3$.CdCl$_2$ | 34.1(34.3) | 3.2(2.7) | 11.3(12.3) | — | 14.2(15.6) | Cd 23.1(24.7) |
| 5 | C$_{13}$H$_{12}$N$_4$O$_3$.1/2CoCl$_2$ | 45.6(46.3) | 3.8(3.6) | 16.1(16.6) | — | 8.9(10.5) | Co 8.3(8.7) |
| 6 | C$_{13}$H$_{12}$N$_4$O$_3$.1/2CuCl$_2$ | 44.4(46.0) | 4.6(3.6) | 13.9(16.5) | — | 8.9(10.4) | Cu 8.0(9.3) |
| 7 | C$_{13}$H$_{12}$N$_4$O$_3$.1/2ZnBr$_2$ | 41.1(40.6) | 3.3(3.1) | 14.5(14.6) | — | Br23.6(20.8) | Zn 7.7(8.5) |
| 8 | C$_{13}$H$_{12}$N$_4$O$_3$.1/2ZnCl$_2$ | 46.0(45.9) | 3.7(3.6) | 16.4(16.5) | — | 10.4(10.4) | — |
| 9 | C$_{14}$H$_{15}$N$_3$OS.CdCl$_2$ | 36.9(36.8) | 3.3(3.3) | 9.5(9.2) | 7.6(7.2) | 15.0(15.5) | Cd 23.9(24.6) |
| 10 | C$_{14}$H$_{15}$N$_3$OS.1/2CuCl$_2$ | 49.3(49.4) | 4.5(4.4) | 12.7(12.3) | 10.0(9.4) | 10.3(10.4) | Cu 10.0(9.3) |
| 11 | C$_{14}$H$_{15}$N$_3$OS.1/2ZnCl$_2$ | 48.9(49.2) | 4.5(4.4) | 12.5(12.3) | 9.6(9.4) | 10.5(10.4) | — |

*The number in parentheses represents the theoretical value as calculated from the Empirical Formula.

EXAMPLE 4

Preparation of
1-(3-pyridylmethyl)-3(4-nitrophenyl)urea cadmium chloride complex 1-(3-Pyridylmethyl)-3-(4-nitrophenyl)urea (2.72 g., 0.01 mole) was dissolved in 40 ml. of hot 2-methoxyethanol and filtered to give a clear solution. To this was added a filtered solution of cadmium chloride (1.83 g., 0.01 mole) in 300 ml. of hot methanol. The reaction mixture was cooled to room temperature to give an off-white precipitate, which was filtered off, washed with 2-methoxyethanol and air dried to give 3.5 g. of white-tan solid. It is a 77% yield of 1-(3-pyridylmethyl)-3-(4-nitrophenyl)urea cadmium chloride complex.

EXAMPLE 10

Preparation of
1-(3-pyridylmethyl)-3-(4-methylthiophenyl)urea cupric chloride complex 1-(3-Pyridylmethyl)-3-(4-methylthiophenyl)urea (2.7 g., 0.01 mole) was warmed in 50 ml. of methanol and filtered to give a clear solution. To this was added a solution of anhydrous cupric chloride (1.3 g., 0.01 mole) in 50 ml. of methanol. A green-blue precipitate immediately formed. More methanol was added so that the solid could be slurried, then the product was filtered off and air dried. The solid was washed with two 100 ml. portions of methanol at 60°C., filtered and air dried over night to give 3.1 g. This is a 91% yield of 1-(3-pyridylmethyl)-3-(4-methylthiophenyl)urea cupric chloride complex.

Table I gives the structure and melting or decomposition points of typical examples of this invention and The 1-(3-pyridylmethyl)-3-(4-substitutedphenyl)urea metal salt complexes of the present invention may be formulated into rodenticidal compositions such as baits, tracking powders, and sprays. A bait comprises a semi-moist or dry edible carrier and the toxicant. The dry carrier is generally preferred and may be a combination of natural food products such as whole ground corn, steel cut oats, sugar, molasses, rice, vegetable oil, salt, dehydrated fruit, fish meal, tankage or wheat. When necessary to use in damp locations, the matrix may be water repellent material such as paraffin wax or an acrylic polymer.

The compounds of the present invention may be incorporated as a toxicant in bait formulations, either alone or in combination with other toxicants. When used as the sole toxicant in baits, the compounds of the present invention may be used in any rodenticidally effective concentration.

Depending on the susceptibility of the rodents to the toxicant and the amount of the formulated bait generally consumed, concentrations as low as 0.1%, and especially when intended for mice, even lower than 0.05% may be employed. A typical bait may contain between about 0.5% and 1.5% of the toxicant by weight and the bait can contain from 0.1 to 99% of the toxicant. An example below describes the formulation of a suitable bait, although wide variations in formulation for different conditions of use are of course expected.

BAIT FORMULATION

A 1-(3-pyridylmethyl)-3-(4-substitutedphenyl)urea metal salt complex was blended with the basal ration in a Waring laboratory blender to form 50 grams of a homogeneous premix. The amount of compound utilized was determined by the percentage of active material desired in the feed. The formula for the basal ration is shown below, all percentages being by weight:

| | |
|---|---|
| Crude ground corn | 65% |
| Steel cut oats | 25% |
| Powdered sugar | 5% |
| Corn oil | 5% |

The 50 grams of premix containing the toxicant were then mixed with an additional 450 grams of basal ration. These components were mixed in a Little Ford Lodige mixer for three minutes.

Tracking powders, which are particularly effective against mice, may be either a compound of the present invention in finely powdered form or a mixture of the compound with powdered carrier, e.g., talc, sugar, milk powder, Indian corn meal, fish meal, cornstarch, flour, and bentonite, or the like, or any combination thereof which tends to induce the animals contaminated with the preparation to lick themselves more thoroughly. In tracking powders, a compound of the present invention may be incorporated in amounts from 100% down to 0.1% by weight with proper formulation. An example below describes the preparation of a suitable tracking powder.

TRACKING POWDER

The active compound is finely pulverized by mortar and pestle to form a 100% active tracking powder. To form a 5% active material, it may be mixed with 10X confectioner's sugar in a 1 to 19 ratio and at other ratios for other levels of active compound.

The compounds were preliminarily evaluated for their ability to kill albino rats (*Rattus norvegicus*) by oral administration to two rats at a dosage of 50–200 mg./kg. In the standard test the effect on the rats is observed over a 14 day period. Table III gives the results with typical examples of this invention.

Table III

| | Preliminary Rodenticidal Activity | | |
|---|---|---|---|
| | Dosage (mg./kg.) | | 18 Mortalities |
| Example | 50 | 200 | No. Dead/Total No. |
| 1 | — | X | 2/2 (5 days) |
| 2 | — | X | 2/2 (24 hrs.) |
| 3 | X | — | 2/2 (6 hrs.) |
| 4 | X | — | 1/2 |
| | — | X | 2/2 (24 hrs.) |
| 5 | X | — | 2/2 (24 hrs.) |
| 6 | X | — | 2/2 (18 hrs.) |
| 7 | X | — | 2/2 (24 hrs.) |
| 8 | X | — | 2/2 (18 hrs.) |
| 9 | — | X | 0/2 |
| 10 | — | X | 2/2 (4 days) |

Table III-continued

| | Preliminary Rodenticidal Activity | | |
|---|---|---|---|
| | Dosage (mg./kg.) | | 18 Mortalities |
| Example | 50 | 200 | No. Dead/Total No. |
| 11 | — | X | 1/2 (3 days) |

An advantage of the metal salt complexes of this invention over the parent 1-(3-pyridylmethyl)-3-(4-substituted-phenyl)-ureas is that they act as a reservoir for the parent rodenticidal urea. It is reasoned that the rodent ingests a lethal amount of the metal salt complex and then death is delayed by the slow release of the urea. In this manner the rodent will disappear from the baiting area and will die in some hide-away; thus, eliminating unsightly dead bodies and creating no unpleasant clean-up problems.

To demonstrate this advantage an evaluation was run on the compounds of this invention as rodenticides using 2 albino rats and an oral dosage level of 20 mg./kg. Comparisons were made with the parent 1-(3-pyridylmethyl)-3-(4-nitrophenyl)urea designated as Cpd. A. The animals were observed closely for four days. The observations made are given in Table IV.

Table IV

| | | | | | Observation[a] | | | | | | | | |
|---|---|---|---|---|---|---|---|---|---|---|---|---|---|
| | | | | | Day 1[b] | | | | | | Day 2 | | Day 4 |
| Example | Complex | 11:25 | 1:05 | 2:10 | 2:40 | 3:20 | 3:45 | 4:20 | 8:00 | 8:05 | 11:25 | 3:30 | 8:00 |
| 3 | Cpd. A. 1/2ZnCl$_2$ | OK | OK | OK | OK | OK | 2 S | 2 S | 2/2 | — | — | — | — |
| 4 | Cpd. A. 1/2CuCl$_2$ | ↓ | ↓ | ↓ | ↓ | ↓ | OK | OK | 1/2 1 S | 1/2 1 S | 1/2 1 S | 1/2 1 S | 2/2 |
| 5 | Cpd. A. CdCl$_2$ | | | | | | OK | OK | OK | OK | OK | OK | OK |
| 6 | Cpd. A. 1/2CaCl$_2$ | | | 1 S | 1 S | 1 S | 1 S | 1/2 | 2/2 | — | — | — | — |
| 7 | Cpd. A. 1/2CoCl$_2$ | | | OK | OK | OK | OK | OK | 2 S | 2 S | 2 S | 2 S | 1/2 1 S |
| 8 | Cpd. A. 1/2ZnBr$_2$ | | | ↓ | ↓ | 1 S | 1 S | 1 S | 2/2 | — | — | — | — |
| | Cpd. A | ↓ | ↓ | 2 S | 2 S | 1/2 1 S | 2/2 | — | — | — | — | — | — |

[a] OK — rats seem normal
S — rat is sick
Mortality — no. of dead rats/total rats in test
dash — observations discontinued
[b] Dosed at 10:00 A.M.

Certain characteristics for an ideal single-dose rodenticide are
1. that it be sufficiently slow in action to allow the rodent to consume a lethal dose,
2. that it not be unpalatable, i.e. free of odor and taste disagreeable to a rodent,
3. that it exhibit no symptoms of poisoning near the bait area which would arouse suspicion in surviving rodents, and
4. that the manner of poisoning should be humane.

The compounds of the present invention fulfill these ideal properties admirably. These metal salt complexes slow down the action of the parent 3-pyridylmethyl 4-substituted-phenyl-ureas sufficiently to accomplish the above purposes, without altering the superb general rodenticidal properties of these parent ureas.

I claim:
1. A compound of the structure

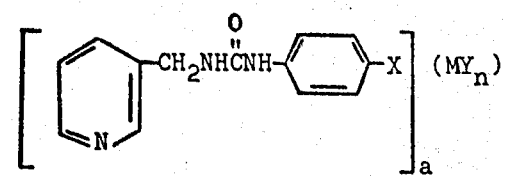

wherein

X is (a) —C(O)R$_1$ wherein R$_1$ is methyl, ethyl or propyl, (b) —SR$_2$, wherein R$_2$ is alkyl of 1 to 4 carbon atoms, or (c) cyano or (d) nitro;

M is a metal ion selected from the group consisting of cadmium, calcium, cobaltous, cupric, nickelous and zinc;

Y is a halide anion;

$a$ is the integer 2 for all cations except cadmium and for this it is 1; and $n$ is an integer corresponding to the valence of M.

2. A compound according to claim 1 wherein X is butyryl.

3. A compound according to claim 1 in which M is calcium, cobaltous, cupric or zinc.

4. A compound according to claim 3 in which Y is bromide or chloride.

5. A compound according to claim 3 in which Y is chloride.

6. A compound according to claim 5 in which M is zinc.

7. The compound of claim 5 which is 1-(3-pyridylmethyl)-3-(4-butyrylphenyl)urea zinc chloride complex.

8. The compound of claim 5 which is 1-(3-pyridylmethyl)-3-(4-cyanophenyl)urea zinc chloride complex.

9. The compound of claim 5 which is 1-(3-pyridylmethyl)-3-(4-nitrophenyl)urea calcium chloride complex.

10. The compound of claim 5 which is 1-(3-pyridylmethyl)-3-(4-nitrophenyl)urea zinc chloride complex.

11. A compound according to claim 1 wherein X is cyano.

12. A compound according to claim 1 wherein X is nitro.

13. A compound according to claim 5 wherein X is methylthio.

* * * * *